(12) United States Patent
O'Connor

(10) Patent No.: US 8,853,635 B2
(45) Date of Patent: Oct. 7, 2014

(54) METHOD AND APPARATUS FOR DUAL-MODALITY ULTRASONIC AND NUCLEAR EMISSION MAMMOGRAPHY

(75) Inventor: Michael K. O'Connor, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/701,754

(22) PCT Filed: Jun. 1, 2011

(86) PCT No.: PCT/US2011/038698
§ 371 (c)(1),
(2), (4) Date: Jan. 8, 2013

(87) PCT Pub. No.: WO2011/153195
PCT Pub. Date: Dec. 8, 2011

(65) Prior Publication Data
US 2013/0101083 A1   Apr. 25, 2013

Related U.S. Application Data

(60) Provisional application No. 61/350,644, filed on Jun. 2, 2010.

(51) Int. Cl.
G01T 1/164 (2006.01)
A61B 6/00 (2006.01)
A61B 6/03 (2006.01)
G21K 1/02 (2006.01)
A61B 8/08 (2006.01)
A61B 6/04 (2006.01)
A61B 8/00 (2006.01)
A61B 19/00 (2006.01)

(52) U.S. Cl.
CPC ............... *A61B 6/502* (2013.01); *A61B 6/4057* (2013.01); *A61B 6/037* (2013.01); *G21K 1/025* (2013.01); *A61B 8/0825* (2013.01); *A61B 6/0414* (2013.01); *A61B 8/4416* (2013.01); *A61B 6/5247* (2013.01); *A61B 6/4291* (2013.01); *A61B 6/4258* (2013.01); *A61B 19/201* (2013.01); *A61B 6/4417* (2013.01)
USPC .................................................... 250/363.01

(58) Field of Classification Search
CPC ............... G01T 2207/30068; A61B 2019/205; A61B 10/0041
USPC .................................. 250/362, 363.01–363.1
See application file for complete search history.

(56) References Cited

U.S. PATENT DOCUMENTS

| | | | |
|---|---|---|---|
| 6,242,743 B1 * | 6/2001 | DeVito et al. | 250/363.05 |
| 6,389,098 B1 | 5/2002 | Keppel et al. | |
| 6,696,686 B1 * | 2/2004 | Wainer et al. | 250/363.1 |
| 6,731,966 B1 | 5/2004 | Spigelman | |
| 2001/0001107 A1 | 5/2001 | Weinberg | |
| 2003/0194050 A1 | 10/2003 | Eberhard et al. | |
| 2003/0197127 A1 | 10/2003 | Wainer et al. | |
| 2008/0208044 A1 | 8/2008 | Lecoq et al. | |
| 2010/0030078 A1 | 2/2010 | Mikami | |
| 2011/0158384 A1 * | 6/2011 | Beekman | 378/37 |
| 2011/0230762 A1 * | 9/2011 | Tokita et al. | 600/437 |

FOREIGN PATENT DOCUMENTS

EP    1 468 651 A1    10/2004

OTHER PUBLICATIONS

Garibaldi F., et al.: "A Novel High Resolution and High Efficiency Dual Head Detector for Molecular Breast Imaging"; Nuclear Science Symposium Conference Record, 2008; NSS '08; IEEE (Oct. 19-25, 2008); IEEE, Piscataway, NJ USA; Oct. 19, 2008; pp. 5647-5649; XP031418793; ISBN: 978-1-4244-2714-7.

C.B. Hruska et al.: "Molecular Breast Imaging: Use of a Dual-Head Dedicated Gamma Camera to Detect Small Breast Tumors"; American Journal of Roentgenology, vol. 191, No. 6; Dec. 1, 2008; pp. 1805-1815; XP055004466; ISSN: 0361-803X; DOI: 10.2214/AJR.07.3693.

S. Meo, et al.: "A dual modality ultrasound-gamma system: first preliminary results of scintigraphic camera"; Nuclear Physics B Proceedings Supplements; 197 (2009); pp. 366-369.

International Search Report and Written Opinion under date of mailing of Dec. 22, 2011 in connection with PCT/US2011/038698.

\* cited by examiner

*Primary Examiner* — Kiho Kim

(74) *Attorney, Agent, or Firm* — Yakov Sidorin; Quarles & Brady LLP

(57) ABSTRACT

A molecular breast imaging ("MBI"} configured for combined MBI and ultrasound imaging or MBI-guided biopsy is provided. In one configuration, the MBI portion of the system includes two opposed gamma ray detectors, while in another configuration only one gamma ray detector is provided. In two detector configurations, a compression plate is provided to make contact with and apply light compression to the subject under examination. One of the gamma ray detectors is configured to be moveable with respect to the other detector such that the gamma ray detector can be moved away from the examination region, thereby allowing access to the breast for an ultrasound imaging system or a breast biopsy device.

20 Claims, 7 Drawing Sheets

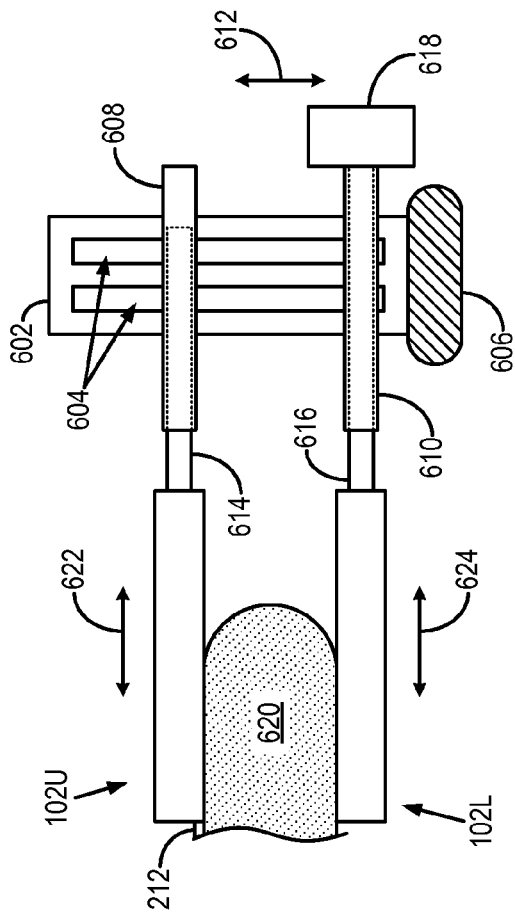
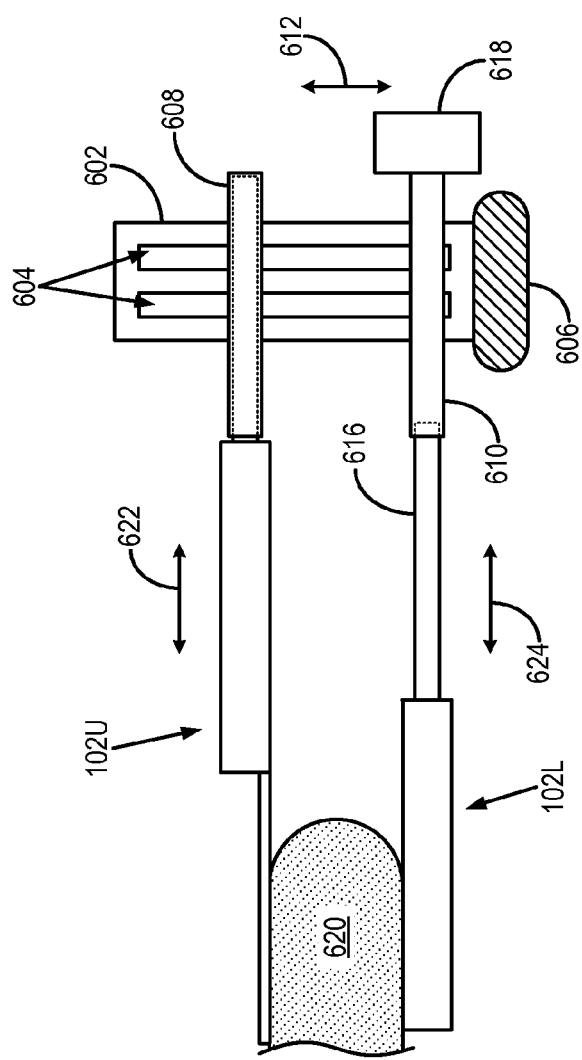
FIG. 6A
FIG. 6B

METHOD AND APPARATUS FOR DUAL-MODALITY ULTRASONIC AND NUCLEAR EMISSION MAMMOGRAPHY

CROSS-REFERENCE TO RELATED APPLICATIONS

This application represents the national stage entry of PCT International Application No. PCT/US2011/038698 filed Jun. 1, 2011, which claims the benefit of U.S. Provisional Patent Application Ser. No. 61/350,644, filed on Jun. 2, 2010, both of which are incorporated herein by reference in their entirety for all purposes.

FIELD OF THE INVENTION

The invention relates to systems and methods for breast imaging. More particularly, the invention relates to systems and methods for combined molecular breast imaging and ultrasound imaging.

BACKGROUND OF THE INVENTION

Breast cancer screening has been recommended for many decades, particularly in women over the age of fifty. The combination of early detection and improved therapy in the U.S. has resulted in a significant reduction in breast cancer mortality, with similar reductions being observed in other countries. Despite the success of screening mammography, however, it is also recognized that mammography is a less than perfect screening method. The limitations of mammography are particularly evident in women with mammographically dense breasts. It has been shown that the sensitivity of mammography decreases with increasing mammographic density, and is less than fifty percent for women with an extremely dense breast pattern on a mammogram.

The reduced sensitivity of mammography with increasing mammographic density is compounded by the fact that increased density is a significant risk factor for breast cancer. Given that a dense breast pattern occurs more frequently in younger women, this factor significantly diminishes the value of mammography in the screening of young women who have a high familial risk of breast cancer.

A second major limitation to screening mammography is in the evaluation of women at high risk of breast cancer. Numerous studies have demonstrated that in women with a high genetic risk of breast cancer, mammography has a sensitivity of between 33-43 percent. Most of these studies have been performed in women with an average age of forty, so part of the explanation for the poor performance of mammography in these studies may be due to the presence of dense breast patterns in a significant percentage of the mammographic images.

A possible solution to the problem of the detection of breast lesions in dense breast tissue is to use ultrasound in such patients. Ultrasound is attractive for supplemental screening because it is widely available, is well-tolerated by patients, and involves no radiation. However, while supplemental ultrasound screening uncovers more breast cancers, it also substantially increases the risk of a false positive cancer finding and unnecessary biopsy. Hence, the use of whole-breast ultrasound as a sole identifier of breast malignancies is questionable. Even in combination with mammography, the two anatomical techniques have significant limitations. It would be of considerable benefit to provide a complementary method that provides functional information about lesions seen on ultrasound. Such a method would significantly reduce the number of false positive cases, and allow the radiologist to evaluate those lesions that demonstrate both a functional and anatomical abnormality.

Over the last five years, several nuclear medicine-based technologies have been developed that have application in breast imaging. Included in these are positron emission mammography ("PEM") and molecular breast imaging ("MBI"). In PEM the breast is compressed between two opposing detectors and the 511 keV gamma rays emitted by a positron emitting radiopharmaceutical, such as F-18 fluoro-deoxyglucose, are detected by coincidence imaging between the two opposing detectors. The PEM images provide an image of glucose utilization by breast tissue and have been shown to be capable of detecting small cancers in the breast. Unlike anatomical techniques such as mammography and ultrasound, PEM is not influenced by dense breast tissue.

The second nuclear medicine-based technique is MBI. This technology employs one or two small gamma cameras. The breast is compressed between a camera and a compression paddle, or between two gamma cameras, and radiation emitted by single-photon radiopharmaceuticals, such as Tc-99m sestamibi, is detected after collimation. MBI is a planar imaging technique without tomographic capability; however, information from two opposing gamma cameras can be used to calculate the true depth of a functional abnormality in the MBI images. The MBI system has been shown to have a very high sensitivity, for example in some cases greater than ninety percent, for the detection of lesions smaller than ten millimeters. In addition, it has been found that, in some cases, MBI can detect three times as many cancers as digital and analog mammography in asymptomatic women at increased risk of breast cancer.

Beyond sensitivity differences, technologies that provide functional images of the breast, such as MBI, can detect lesions not visible with conventional mammography. Likewise, certain benign breast conditions may result in a false positive finding on MBI, and this uptake can be readily identified as a benign process from the anatomical information available in ultrasound. Currently it is not practical to fuse anatomical images from ultrasound systems and functional images from MBI. Ultrasound requires that the patient lie supine and a handheld scanner is then used to scan the breast. MBI is usually performed with the patient seated and the breast lightly compressed between the gamma cameras or camera and paddle. MBI employs light compression forces, for example 10-15 pounds of force, with imaging times in the 5-10 minute range. The imaging procedure is generally considered to be substantially pain-free. Because of the differences in patient orientation between MBI and ultrasound, the shape of the breast tissue is significantly different between the two modalities and, hence, correlation of an anatomical abnormality with a functional abnormality becomes difficult. Therefore, accurate co-registration of anatomical images from ultrasound and functional information from MBI is not currently possible.

Over the last few years, several entities have worked on the development of whole-breast ultrasound ("WUS") systems. The main purpose of this development was to reduce the dependence of image quality on the technologist or radiologist, and provide a more reproducible imaging technique. These systems are designed to image the patient in the supine position in a comparable manner to conventional breast ultrasound. If the patient is not supine, then the WUS system suffers from a loss in the achievable coverage of the breast tissue. Therefore, while WUS systems provide better coverage in non-supine patient positions than traditional ultrasound imaging, they are still limited in their applicability to combination with imaging modalities that require non-supine patient positions, such as MBI.

It would therefore be desirable to provide an MBI system that would allow the acquisition of both anatomical and functional images of the breast, such images being amenable to co-registration so that accurate and reliable assessments of the presence of cancerous lesions in the breast can be made. Additionally, it would be desirable to provide an MBI system that would also allow for breast biopsies to be performed under the guidance of MBI.

SUMMARY OF THE INVENTION

The present invention overcomes the aforementioned drawbacks by providing a molecular breast imaging ("MBI") that is configured for combined MBI and ultrasound imaging or combined MBI and image-guided breast biopsy. Generally, the MBI system includes two opposed gamma ray detectors, in which one of the gamma ray detectors is configured to be moveable with respect to the other such that one gamma ray detector can be moved away from an examination region, thereby permitting ultrasound imaging or image-guided breast biopsy.

It is an aspect of the invention to provide an MBI system that includes a support structure arranged proximate to an examination region, a first detector head coupled to the support structure to extend along a first portion of the examination region, and a second detector head coupled to the support structure to extend along a second portion of the examination region. The first detector head includes a first gamma ray detector supported by the support structure and extending to define a first imaging plane proximate to the examination region, and a first collimator extending substantially coplanar with the first imaging plane and arranged between examination region and the first detector. Likewise, the second detector head includes a second gamma ray detector supported by the support structure and extending to define a second imaging plane proximate to the examination region, and a second collimator extending substantially coplanar with the second imaging plane and arranged between examination region and the second detector. The MBI system further includes an adjustable coupling arranged between the first detector head and the support structure. The adjustable coupling permits movement of the first detector head between a first position, in which the first detector head is substantially directly opposed to the second detector head, and a second position, in which the first detector head is not substantially directly opposed to the second detector head.

It is another aspect of the invention that the adjustable coupling may be a pivot that defined a rotational axis to permit the first detector head to rotate about the rotational axis to move the first detector head between the first position and the second position.

It is yet another aspect of the invention that the adjustable coupling may be a support arm that is configured to slidably move the first detector head along a direction lying in the first imaging plane to permit the first detector head to move along the direction, thereby moving the first detector head between the first position and the second position.

It is yet another aspect of the invention provide a collimator amenable for image-guided breast biopsy. Such a collimator may include a first collimator section having septa extending along a first direction and a second collimator section having septa extending along a second direction. The first collimator section may be a parallel-hole collimator section in which the first direction is substantially perpendicular to the second imaging plane, and the second collimator section may be a slant-hole collimator section, in which the second direction is angled with respect to the second imaging plane at an angle between zero and ninety degrees. The parallel-hole collimator section may have a substantially circular outer periphery, and the slant-hole collimator section may be annular in shape and be arranged to extend about the outer periphery of the parallel-hole collimator section. For example, the collimator may be the second collimator of an MBI system, or may be used in single detector systems.

It is yet another aspect of the invention that the second detector head of the MBI system may include a collimator sleeve coupled to the second gamma ray detector and configured to interchangeably receive the second collimator.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6A is an illustration of a configuration of an exemplary pair of gantry-mounted opposed gamma detector heads that form a part of an MBI system, in which the opposed gamma detectors are configured to move longitudinally relative to one another;

FIG. 6B is an illustration of the exemplary pair of gantry-mounted opposed gamma detector heads of FIG. 6A showing one gamma detector head in a retracted position and another gamma detector head in an extended position;

DETAILED DESCRIPTION OF THE INVENTION

Current schemes for radio-guided breast biopsy are limited in their ability to incorporate additional information from x-ray or ultrasound imaging. Additionally, such schemed only provide a mechanism to localize a lesion and to perform biopsy, but do not provide any supplementary information about the lesion. Thus, the schemes developed for positron emission mammography ("PEM") and breast specific gamma imaging ("BSGI") only provide a conventional imaging scheme to localize a lesion, and neither of these systems incorporates any innovative features to enhance or accelerate the biopsy process. With typical imaging times for both PEM and BSGI at around ten minutes per view, the biopsy process can become a lengthy procedure depending on how many images need to be acquired to confirm correct placement of the biopsy needle.

The MBI system of the present invention provides anatomical correlation information, which is very helpful for aiding a clinician in the decision making process. In breast imaging, the variability in breast position between different modalities can make it difficult to correlate findings across these modalities, particularly in complex cases where both benign and malignant tissue regions may be present. It is contemplated that the ability to co-register an area of increased uptake on an image obtained with MBI with the corresponding area on an ultrasound image will enable physicians to better determine the nature of the lesion and the appropriate course of action.

The MBI system of the present invention may include one of a number of specially designed collimators that are designed to improve the sensitivity of the MBI system when a priori knowledge of the location of the lesion is available. These collimators do not need to image the entire breast, but can instead be focused on the area of the breast around the lesion. These focused collimators enable a substantial gain in MBI system sensitivity without loss of spatial resolution, but require that the focused collimators be positioned under the lesion. A mechanism is also provided that enables rapid and easy translation of a collimator to the appropriate region of the breast.

Figure 1:
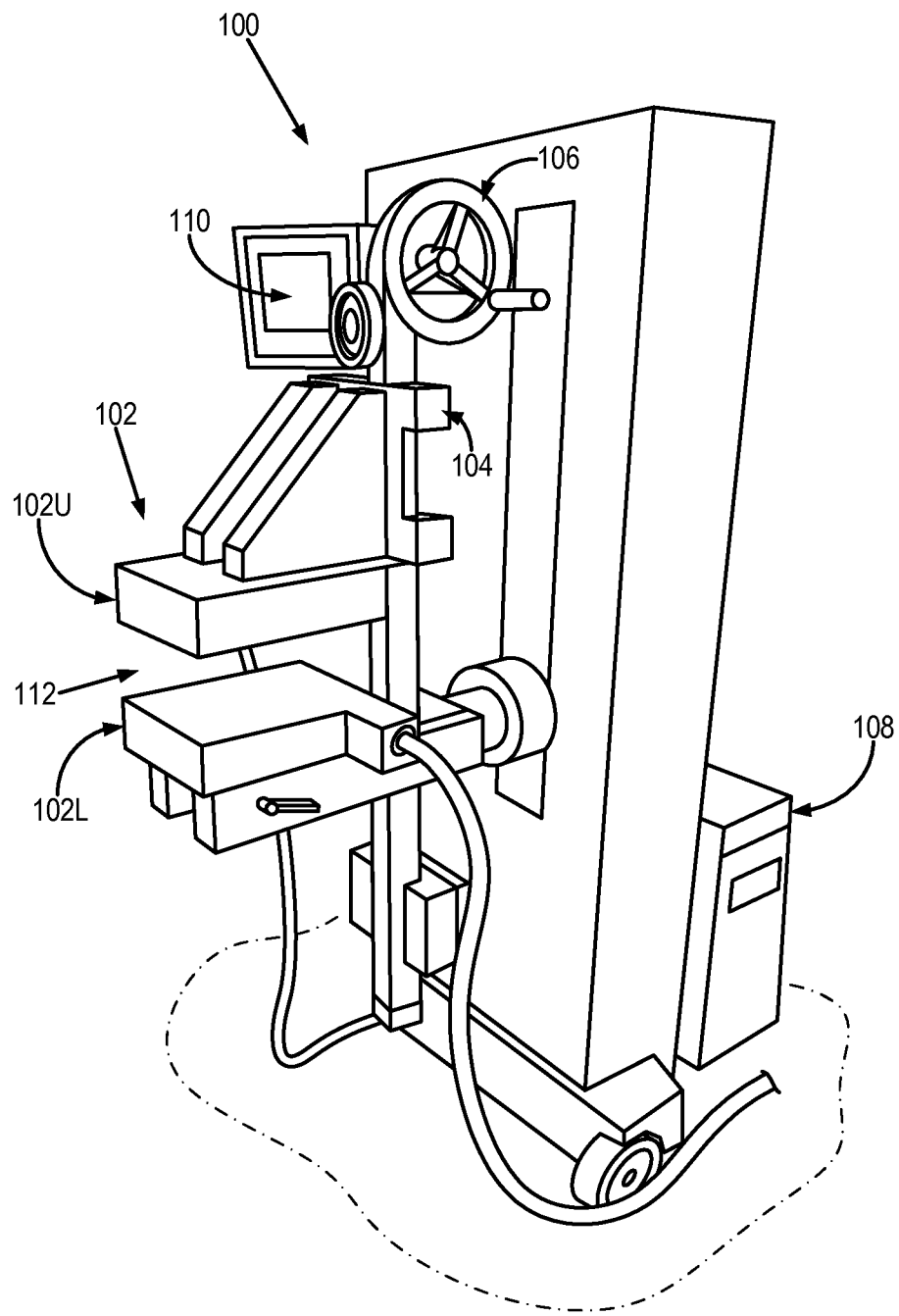
FIG. 1 is an illustration of an exemplary molecular breast imaging ("MBI") system for use with the present invention.

Referring to FIG. 1, a molecular breast imaging ("MBI") system 100 includes two opposing cadmium zinc telluride ("CZT") detectors, shown as detector heads 102. In particular, the detector heads 102 include an upper detector head 102U and a lower detector head 102L. Exemplary MBI systems and methods for their use are described, for example, in co-pending U.S. patent application Ser. No. 12/515,369, entitled "System and Method for Quantitative Molecular Breast Imaging," which is herein incorporated by reference in its entirety. Each detector head 102U, 102L may be, for example, 20 centimeters ("cm") by 16 cm in size and mounted on a modified upright type mammographic gantry 104. In one configuration, the detector heads 102 are Lumagem® 3200S high-performance, solid-state cameras from Gamma Medica-Ideas, Inc., having a pixel size of 1.6 millimeters ("mm") (Lumagem® is a trademark of Gamma Medica-Ideas, Inc., Northridge, Calif.).

The relative position of the detector heads 102 can be adjusted using a user control 106. Specifically, the detector head assemblies 102 are, preferably, designed to serve as a compression mechanism. Accordingly, this system configuration reduces the maximum distance between any lesion in the breast and either detector head 102 to one-half of the total breast thickness, potentially increasing detection of small lesions without additional imaging time or dose. The MBI system 100 includes a processor 108 for processing the signals acquired by the detector heads 102 to produce an image, which may be displayed on an associated display 100.

In general, the detector heads 102U, 102L are arranged so as to form an examination region 112 therebetween. The examination region 112 is defined with respect to a first imaging plane and a second imaging plane. The first imaging plane is defined, for example, by the extension of the upper detector head 102U along the examination region 112, and the second imaging plane is defined, for example, by the extension of the lower detector head 102L along the examination region 112.

It is a teaching of the present invention that one of the detector heads 102 of an MBI system can be configured to provide an MBI system amenable to combined MBI and ultrasound imaging, or combined MBI and breast biopsy. In other configurations, one of the detector heads 102 can be replaced with an ultrasound probe or a WUS imaging apparatus particularly configured for use with the MBI system. In general, configurations of an MBI system that are amenable for combined MBI and ultrasound imaging, or combined MBI and breast biopsy, include detector heads 102 that can be moved relative to one another such that the breast becomes accessible for an ultrasound imaging system or biopsy device. Thus, in general, the MBI system may include a first detector head that is configured to move between a first position and a second position relative to a second detector head. Generally, such a first position would be one in which the two detector heads are opposed and configured for MBI, and such a second position would be one in which the two detector heads are no longer opposed, thereby providing access to the breast for ultrasonic imaging or biopsy. For example, the upper detector head 102U may be configured to rotate away from the lower detector head 102L, or, the detector heads 102 may be configured to move longitudinally relative to one another.

In general, such a system will provide a more complete imaging solution for women with dense breast tissue where the sensitivity of mammography is know to be limited, and will do so in a cost-effective manner that should permit its widespread adoption into clinical practice.

Figure 2:
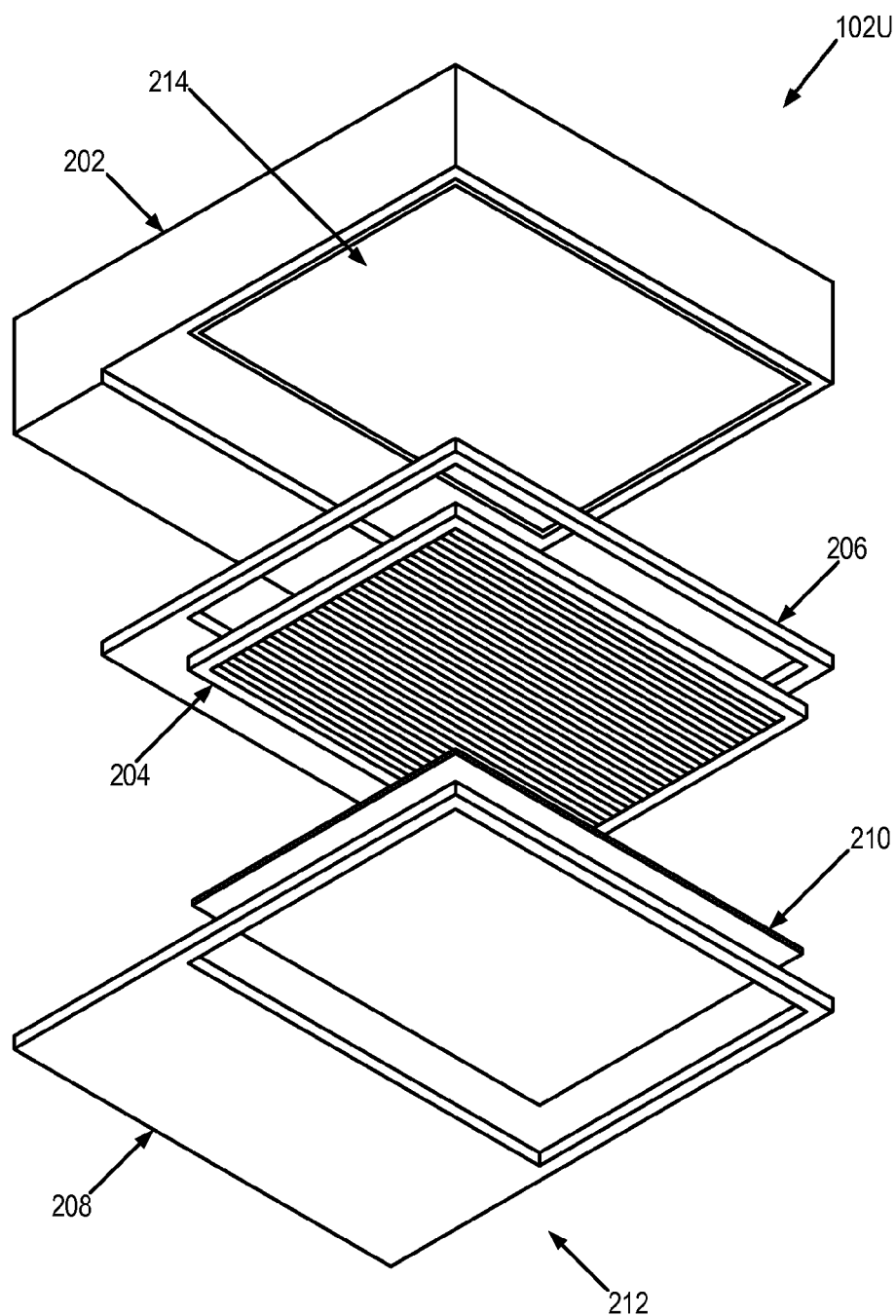
FIG. 2 is an exploded view of an exemplary gamma detector that forms a part of the MBI system of FIG. 1 and is configured for use with an ultrasound probe or an automated whole-breast ultrasound ("WUS") system.
Figure 3:
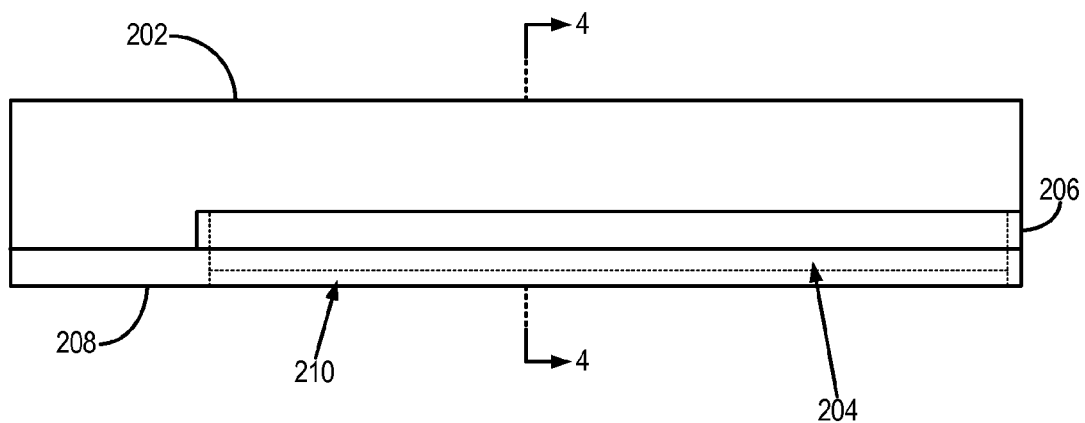
FIG. 3 is an elevation view of the exemplary gamma detector of FIG. 2.
Figure 4:
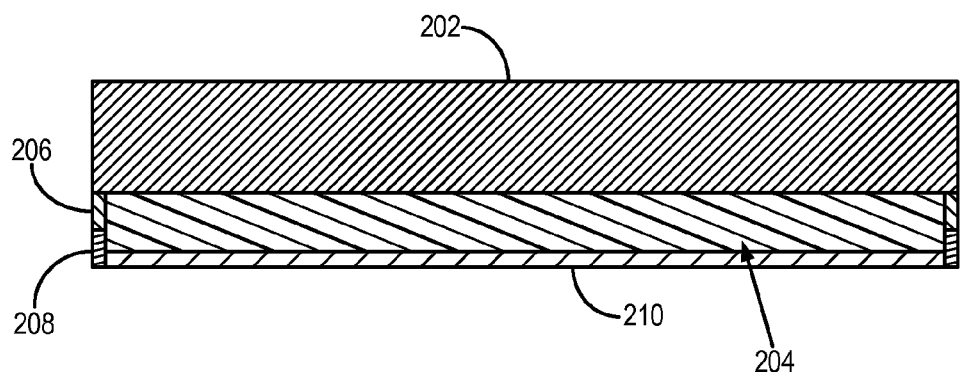
FIG. 4 is a cross-section of the exemplary gamma detector of FIG. 3.

An exemplary configuration of a detector head 102, such as an upper detector head 102U, that is configured for combined MBI and ultrasound imaging, or that is amenable for MBI guided breast biopsy, is illustrated in FIGS. 2-4, to which reference is now made. The detector head 102 includes a gamma ray detector 202, a collimator 204, and an inner collimator frame 206. The gamma ray detector 202 and collimator 204 are arranged such that the collimator 204 is substantially parallel to the imaging plane defined by the detector head 102. The detector head is positioned over an outer collimator frame 208 and an acoustic coupling plate 210. Together, the outer collimator frame 208 and acoustic coupling plate 210 may be referred to as a compression plate 212. Other configurations of a compression plate 212 may include only the acoustic coupling plate 210, an acoustic coupling plate 210 coupled to one or more support members, or a biopsy grid plate coupled to an outer frame, such as the outer collimator frame 208. The inner collimator frame 206 is sized to be received by a recessed portion of the detector head 102. The inner collimator frame 206 is further sized on its inner extent to receive the collimator 204, such that the collimator is positioned in alignment with a detector array 214 formed on a surface of the gamma ray detector 202. By way of example, the detector array 214 may be composed of cadmium zinc telluride ("CZT") detector elements. The outer collimator frame 208 is sized on its inner extent to receive the acoustic coupling plate 210 and the collimator 204, such that the collimator 204 comes into contact with the acoustic coupling plate 210. The acoustic coupling plate 210 is positioned within the outer collimator frame 208 such that the acoustic coupling plate 210 forms a substantially flush surface with the outer collimator frame 208, thereby providing a contact surface for receiving and compressing a portion of a subject under examination, such as a portion of the subject's breast.

The acoustic coupling plate 210 is composed of a material with low attenuation, and is preferably composed of a material with similar ultrasonic reflective properties as soft tissue. Exemplary materials include nylon and latex. The acoustic coupling plate 210 may also be constructed so as to permit the passage of a biopsy needle through the acoustic coupling plate 210 and into the breast. For example, a nylon mesh can be employed and manufactured with a hole grid to allow a needle to be passed through for biopsy. Additionally, the acoustic coupling plate 210 permits the breast to be retained in a compressed position prior to retraction of the detector head 102.

In ultrasound imaging applications, the precise location of a lesion imaged by the lower detector head 102L can be used to position an ultrasonic probe and permit co-registration of the MBI and ultrasonic images. This may be facilitated by marking the acoustic coupling plate 210, for example, with a grid pattern that can be labeled to match locations on the MBI images. The location of the lesion identified from an MBI image can also be entered into the ultrasound system and an electronic mark on the ultrasound image used to direct and confirm co-registration of the MBI and ultrasound information.

For MBI-guided biopsy applications, the acoustic coupling plate 210 may be replaced by a rigid frame that accommodates a biopsy grid plate, through which a biopsy may be performed. Exemplary biopsy frames are designed to accommodate disposable biopsy grid plates, such as those used in commonly available biopsy devices including the Mammotome Biopsy System (Mammotome, Cincinnati, Ohio) and the ATEC system (Hologic, Inc., Bedford, Mass.).

Current MBI gantry designs work adequately for conventional breast imaging, but do not easily accommodate the integration of an MBI system with another imaging modality, or the introduction of a biopsy device. Thus, the provided MBI system is designed to include detector heads 102 that can be moved so as to provide access to the subject's breast, whether for ultrasound imaging or biopsy.

Figure 5:
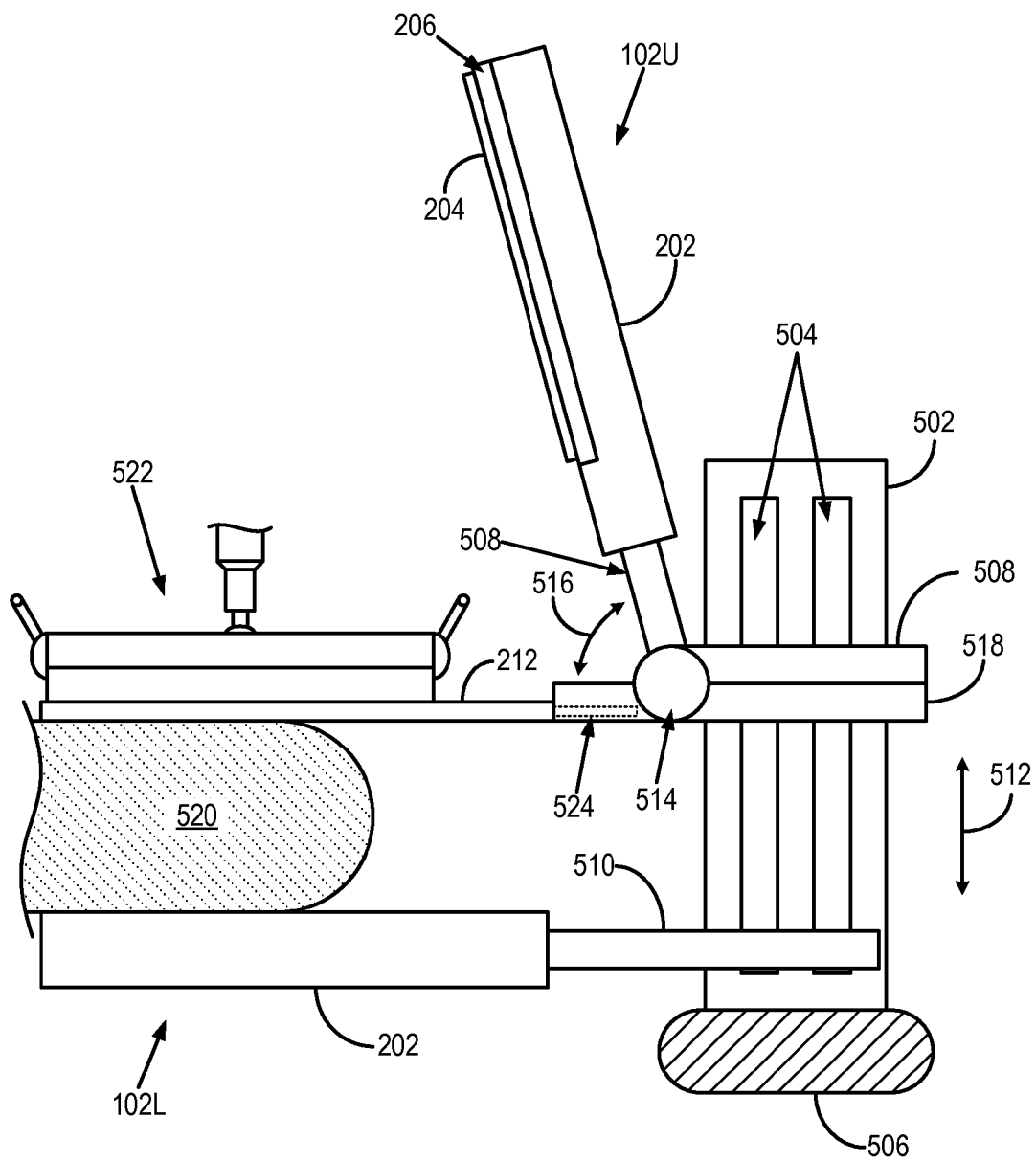
FIG. 5 is an illustration of a configuration of an exemplary pair of gantry-mounted opposed gamma detector heads that form a part of an MBI system, in which one gamma detector head is configured to be rotated away from another gamma detector head.

Referring now to FIG. 5, an exemplary configuration of an MBI system having a gantry-mounted, hinged upper detector head 102U that can be rotated away from the lower detector head 102L so as to provide access to the subject's breast for ultrasound imaging or biopsy is illustrated. The MBI system 500 includes a support structure 502 having formed therein one or more tracks 504. The support structure 502 is coupled to a gantry 506 that allows for the MBI system 500 to be positioned about the patient in a number of different orientations. Coupled to the tracks 504 are an upper support arm 508 and a lower support arm 510. The upper detector head 102U is coupled to the upper support arm 508, and the lower detector head 102L is coupled to the lower support arm 510. A motor (not shown in FIG. 5) drives the upper support arm 508 so that the upper detector head 102U is moved along a direction 512 towards or away from the lower detector head 102L. The upper support arm 508 includes a hinge 514 that allows the upper detector head 102U to be rotated away from the lower detector head 102L about a rotational axis of the hinge 514 and along a rotation direction 516. The upper support arm 508 may be coupled to an additional compression support arm 518. When the upper support arm 508 and the compression support arm 518 are together, the compression support arm 518 is used to achieve breast compression with the upper detector head 102U.

The aforementioned hinge 514 is but one example of an adjustable coupling between one detector head 102, such as the upper detector head 102U, and the support structure 502. Generally, this adjustable coupling permits movement of the coupled detector head with respect to the other detector head. More generally, the adjustable coupling permits movement of one detector head between a first position and a second position relative to the other detector head. For example, the first position may be one in which the two detector heads are substantially directly opposed, and the second position may be one in which the two detector heads are not substantially directly opposed to each other. For the configuration illustrated in FIG. 5, in the first position the imaging planes defined by the two detector heads are substantially parallel, and in the second position the imaging plane defined by the upper detector head 102U would be angled away from the imaging plane defined by the lower detector head 102L. In one example, the imaging plane defined by the upper detector head 102U would be rotated such that it is substantially perpendicular to the imaging plane defined by the lower detector head 102L. It should also be appreciated that the hinge 514 that forms an adjustable coupling may also be configured so that the axis of rotation is perpendicular to the imaging plane defined by the coupled detector.

Functional imaging of the breast is performed using the aforementioned MBI system, which permits a calculation of an in-plane location of a lesion in the breast, as well as its depth and relative uptake of an administered radionuclide. Following completion of the MBI acquisition, the upper detector head 102U may be withdrawn, leaving the compression plate 212 in place. By rotating the gamma camera in the upper detector head 102U, the compression plate 212 remains in physical contact with the subject's breast 520. This process allows the maintenance of constant compression of the breast 520 between the lower detector head 102L and the compression plate 212 while the MBI system converts from a molecular imaging mode to an ultrasound imaging or biopsy mode. Moreover, this constant compression of the breast 520 mitigates subject movement while switching between operational modes.

After the upper detector head 102U is rotated away from the breast 520, an ultrasound system 522 may replace the upper MBI detector to either perform a sweep across the breast to obtain three-dimensional images of the breast tissue, or to obtain high resolution images of an area of concern identified on the MBI images. While a WUS system is illustrated in FIG. 5, a conventional hand-held ultrasound transducer may also be used. Upon completion of both the molecular and ultrasound imaging acquisitions, the MBI and ultrasound images are co-registered. Using the MBI system configuration illustrated in FIG. 5, functional and anatomical information are obtained sequentially from the two imaging modalities. As a result, some motion or movement of the breast may occur between the two imaging processes; however, these errors can be addressed during co-registration of the images.

This MBI system configuration is benefited in that the location of a lesion not visible on conventional ultrasound can be determined and indicated on the MBI image, and may also be identifiable from enhanced ultrasonic techniques, such as elastography, thereby permitting ultrasound-guided biopsies if desired. In a high percentage of cases, for example greater than eighty percent, a lesion can be seen on just the lower MBI detector; thus, during ultrasound imaging, information on the location of the lesion can be updated on the ultrasound system to confirm that the location of a lesion has not shifted in the conversion from MBI to ultrasound imaging modes, which can also be useful for addressing inter-imaging motion errors.

The gantry 506 may be designed to be compatible with a biopsy table, such as the DBI Table (Medical Positioning Inc., Kansas city, Mo.). Such a table allows the patient to lie on her side with the superior breast positioned in the MBI system.

The back support and patient position minimizes motion and enables better access into the axillary tail and posterior-lateral breast.

Depending on the configuration of the upper support arm 508 and compression support arm 518, the compression plate 212 can be configured to attach to the compression support arm 518, for example by "plugging" the compression plate 212 into appropriately sized holes in the compression support arm 518, as illustrated at arrow 524 in FIG. 5.

Referring now to FIGS. 6A and 6B, another exemplary configuration of an MBI system having a gantry-mounted upper detector head 102U and lower detector head 102L, which can be slidably moved relative to each other so as to provide access to the subject's breast for ultrasound imaging or biopsy, is illustrated. Like the configuration illustrated in FIG. 5, the configuration illustrated in FIGS. 6A and 6B include an adjustable coupling that permits movement of one detector head between a first and second position relative to another detector head. However, in the configuration illustrated in FIGS. 6A and 6B, this adjustable coupling includes support arms coupled to the support structure that allow movement of the detector heads along a direction that is coplanar with the respective imaging planes defined by the detector heads. FIG. 6A illustrates the MBI system in such a first position, and FIG. 6B illustrates the MBI system in such a second position. Like the MBI system configuration illustrated in FIG. 5, this MBI system configuration includes a support structure 602 having formed therein tracks 604. The support structure 602 is coupled to a gantry 606 that allows for the MBI system 600 to be positioned about the patient in a number of different orientations. Coupled to the tracks 604 are an upper support arm 608 and a lower support arm 610. The upper detector head 102U is coupled to the upper support arm 608, and the lower detector head 102L is coupled to the lower support arm 610. A motor (not shown in FIG. 6) drives the upper support arm 608 so that the upper detector head 102U is moved along a direction 612 towards or away from the lower detector head 102L.

The upper support arm 608 includes a retractable arm 614 that is coupled on one end to the upper detector head 102U and on the other to the upper support arm 608. Likewise, the lower support arm 610 includes a retractable arm 616 that is coupled on one end to the lower detector head 102L and on the other to the lower support arm 610. The retractable arms 614, 616 allow the upper detector head 102U and the lower detector head 102L to be slidably moved relative to each other. In the illustrated configuration, the upper detector head 102U may be moved along a longitudinal direction 622 towards or away from the support structure 602, and the lower detector head may be moved along a longitudinal direction 624 towards or away from the support structure 602. During an imaging procedure in which the physician desires to gain access to the breast 620, either for ultrasound imaging or to perform a biopsy, the upper detector head 102U may be moved towards the support structure 602 by retracting the retractable arm 614 within the upper support arm 608. At the same time, the lower detector head 102L may be moved away from the support structure 602 by extending the retractable arm 616 out of the lower support arm 610. A counterweight 618 is attached to the lower support arm 610 on the end opposite the lower detector head 102L so that when the lower detector head 102L is in its extended position, the MBI system 600 remains balanced and stable. In this MBI system configuration, the compression plate 212, including an acoustic coupling plate 210 or biopsy frame, may be coupled to the upper detector head 102U such that it is substantially parallel to the imaging plane defined by the upper detector head 102U, as illustrated in FIGS. 6A and 6B.

Figure 7:
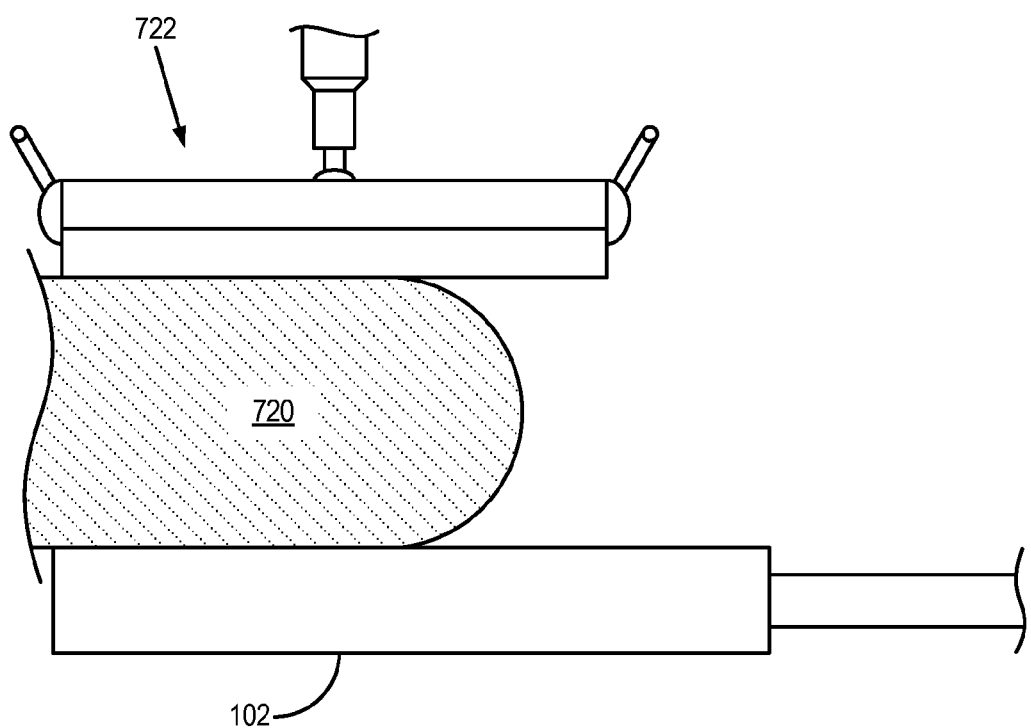
FIG. 7 is an illustration of an exemplary gamma detector head that forms a part of an MBI system configured for use with an ultrasound probe or an automated WUS system.

Referring now to FIG. 7, another exemplary configuration of a combined MBI-ultrasound system includes an ultrasound system, such as a WUS system, 722 having an ultrasound paddle of similar dimensions to an MBI detector head 102. Exemplary WUS systems include a combined ultrasound probe and compression paddle device marketed under the trademark SomoVu™ (U-Systems, Sunnyvale, Calif.). The ultrasound system 722 is normally designed to be placed directly on the breast tissue with the patient supine. The operator can then perform an automated scan of the breast. In the described configuration of the MBI system, the WUS paddle acts as one part of a compression device to lightly compress breast tissue between the WUS paddle and an MBI detector 102. This configuration of the MBI system also includes an MBI detector head 102 including a single gamma camera that can be positioned underneath the breast 720.

Another exemplary configuration of a combined MBI-ultrasound system includes the capability for elastography on the ultrasound system. Exemplary systems include an ultrasound probe with elastography capability marketed under the trademark Aixplorer™ (SuperSonic Imagine, Aix-en-Provence, France). The Aixplorer is normally designed to be placed directly on the breast tissue with the patient supine. In the described configuration of the MBI system, the Aixplorer probe is placed on top of the acoustic coupling plate 210, and shearwave elastography is performed over the region of abnormal uptake identified in the MBI images. This configuration of the MBI system also includes an MBI detector head 102 including a single gamma camera that can be positioned underneath the breast 720.

In use, the patient is seated and the breast lightly compressed by the WUS paddle and MBI detector 102, in a similar orientation to mammography. Functional imaging of the breast is performed using the MBI system and simultaneously the WUS system 722 can complete a sweep across the breast 720 to obtain 3D images of the breast tissue. Upon completion of both image acquisitions, the MBI and WUS images are co-registered. Advantages of this configuration include reduced scan time due to the simultaneous acquisition of both the MBI and WUS images, and reduced likelihood of motion artifact causing misregistration. On the other hand, this configuration does not provide depth information, and can instead provide only the in-plane location of a lesion for co-registration with the WUS image. Thus, the lesion must also be visible on WUS in order to determine exact location if ultrasound-guided biopsy is planned or desired.

When performing an MBI-guided biopsy procedure, the standard obturator may be replaced with one modified to contain a small radioactive marker so that the biopsy needle is discernable on MBI images. The marker may be composed of an Iodine-125 ("I-125") seed. The low gamma ray energy of I-125 emissions, which is on the order of 27 keV, ensures that emissions from the marker will not interfere with the Tc-99m sestamibi image obtained from the patient. This marker can be imaged when using, for example, CZT detectors, which are capable of imaging from 15-500 keV emissions. The location of the lesion on the MBI image from the lower detector head 102L will be used to determine the in-plane coordinates for the biopsy needle. While an estimate of the lesion depth can be used from the initial dual-head images, a problem with performing a biopsy under this condition is that the location of the lesion may shift during the biopsy process. Hence, it is advantageous to configure the MBI system for real-time imaging to insure up-to-date information is available with regard to the exact location of the lesion during the biopsy process.

To facilitate image-guided breast biopsy, a specially designed collimator may be used to improve the sensitivity of the MBI system, or other nuclear medicine-based imaging systems, by an order of magnitude. An exemplary collimator of this nature is composed, for example, of two sections: a first collimator section having septa that extend along a first direction, and a second collimator section having septa that extend along a second direction. By way of example, the first collimator section may be a parallel-hole collimator section having septa that extend substantially along a direction perpendicular to an imaging plane defined by the collimator and gamma ray detector; and the second collimator section may be a slant-hole collimator having septa that extend along a direction that is angled with respect to the imaging plane, such as at an angle of sixty degrees from the imaging plane.

Figure 8A:
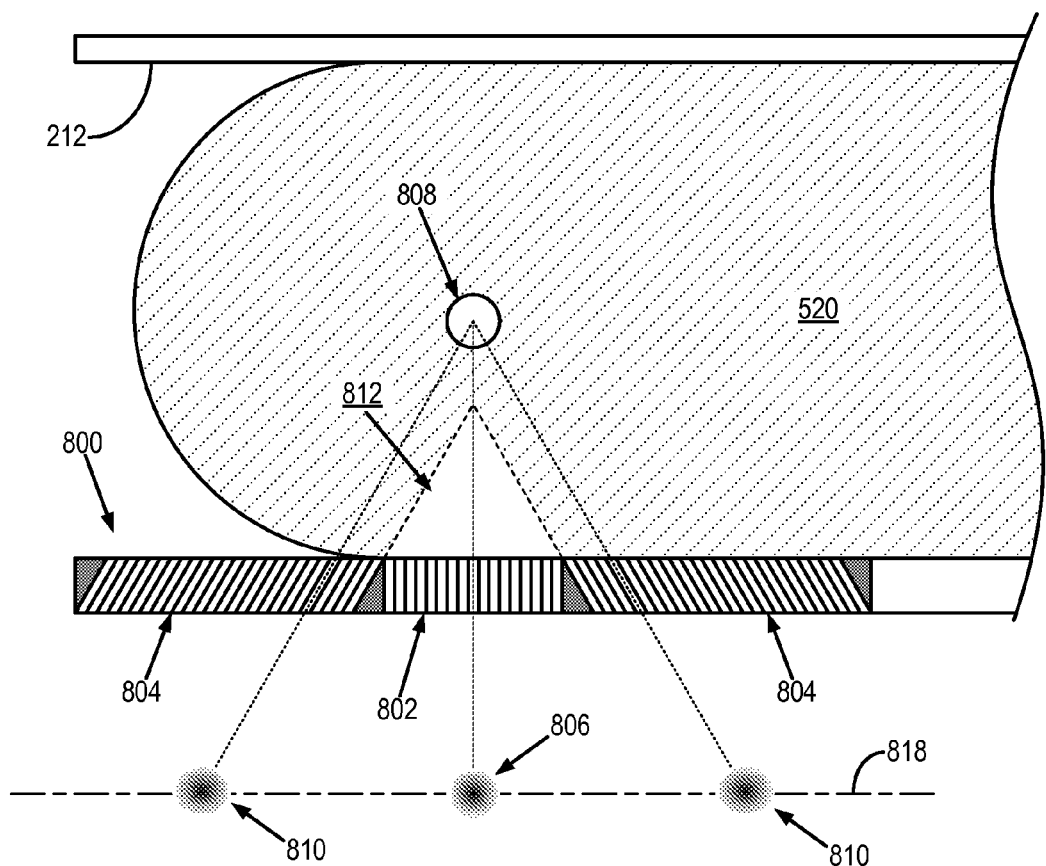
FIG. 8A is an illustration of an exemplary collimator for use during image-guided breast biopsies.

By way of example, a cross-sectional view of one configuration of an exemplary collimator having a first collimator section and a second collimator section is illustrated in FIG. 8A. In the illustrated configuration, the collimator 800 includes a parallel-hole section 802 and a conical slant-hole section 804. The conical slant-hole section 804 may be angled at, for example, sixty degrees with respect to an imaging plane 818 defined by the collimator 800 and a gamma ray detector (now show in FIG. 8). In this configuration, the second collimator section is generally oriented about a periphery of the first collimator section. For example, the parallel-hole collimator section 802 may be circular in shape and the slant-hole collimator section 804 may be annular in shape with the septa in the slant-hole collimator section 804 angled towards the parallel-hole collimator section 802. The parallel-hole section 802 enables confirmation that the collimator 800 has been appropriately positioned below the lesion and reduces the likelihood that a biopsy needle will penetrate through the lower side of the breast, thereby impacting the collimator 800.

The parallel-hole section 802 will produce a parallel-hole image 806 of a lesion 808. When the lesion 808 is a sufficient distance away from the collimator 800, the lesion will also produce multiple slant-hole images 810. If the lesion 806 produces a parallel-hole image 806, but no slant-hole images 810, then it is too close to the collimator 800. In such an instance, a biopsy needle may penetrate through the breast, thereby contaminating the needle with lead from the collimator 800 and introducing these contaminants into the breast 520. Thus, any lesion producing only a parallel-hole image 806, and no slant-hole images 810 will be considered to be located too close to the lower detector head 102L for safe performance of a biopsy. In this case, the lower detector head 102L can be repositioned so that the lesion 808 is not in as close proximity to the lower detector head 102L. The angle of the slant holes in the slant-hole collimator section 804 and the diameter of the parallel-hole collimator section 802 define the size and shape of a region 812 in which a lesion is considered to be too close to the collimator for the safe performance of a biopsy. When a lesion is positioned within this region 812, the lesion will not produce slant-hole images, indicating that the lesion is too close to the collimator 800 for safe performance of a biopsy.

In the illustrated configuration, the diameter, D, of the parallel-hole section 802 is determined by the equation:

$$D = 2h \cdot \tan(\theta) \quad (1);$$

where h is the height of the region 812, and θ is the hole angle of the slant-hole collimator section 804. By way of example, to provide a region 812 with a height of 2 cm, and given a hole angle of thirty degrees, the diameter, D, of the parallel-hole collimator section 802 should be set at 2.3 cm. Using this collimator design, a lesion seen as a small hot spot in the parallel-hole image 806 will be viewed as a ring of activity in the slant-hole images 810. Tumor depth can be calculated from the diameter of the parallel-hole collimator section 802.

Figure 8B:
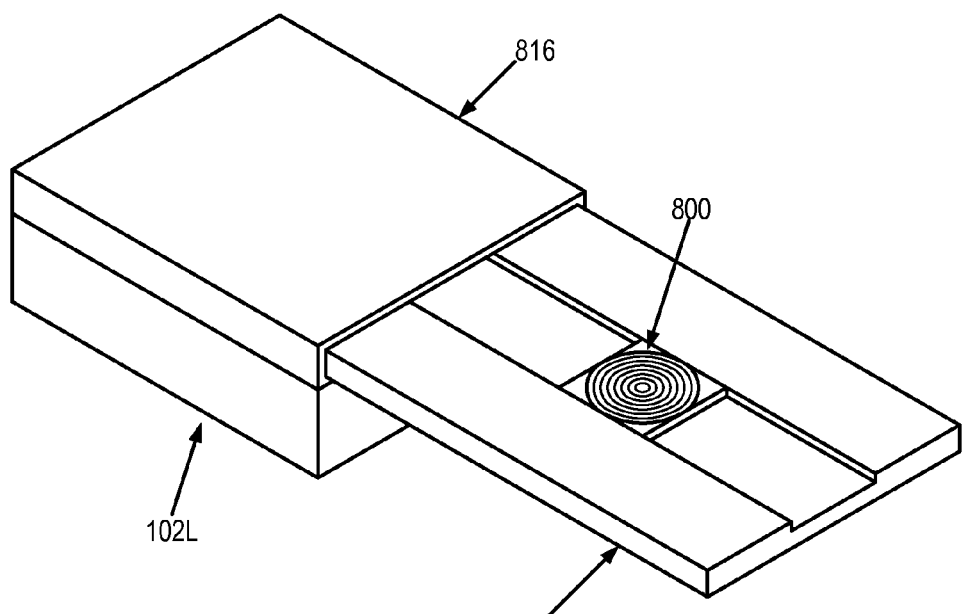
FIG. 8B is a pictorial representation of the exemplary collimator of FIG. 8A placed in an exemplary collimator sleeve that is coupled to a gamma ray detector head, such as one that forms a part of an MBI system.

Because the aforementioned collimator 800 must be positioned beneath a lesion in order to visualize it, the collimator 800 may be mounted on a tray 814 that can slide into a collimator sleeve 816 that is coupled to the lower detector head 102L, as illustrated in FIG. 8B. Lead or tungsten plates may be used to limit the detector field-of-view to the area of the collimator 800. The tray 814 can slide into the collimator sleeve 816 and be positioned beneath the lesion 808. Using this arrangement, different types of collimator designs can be accommodated. For example, collimators having parallel-hole sections of different diameters, or slant-hole portions with different angles, may be constructed and interchanged from the tray 814 depending on the imaging application. Likewise, conventional parallel-hole collimators may also be positioned in the tray 814 as needed. In this manner, different breast thicknesses can be easily accommodated by the same MBI system. By way of example, for a breast thickness of up to 6 cm, the collimator should be on the order of 6.9 cm in width, and for breast thicknesses greater than 6 cm, the collimator should be constructed with a shallower hole angle to ensure visualization of deep lesions while still maintaining a fixed collimator size of around 7 cm in width.

In clinical use, the aforementioned conical collimator would be positioned underneath the lesion to be biopsied. For lesions close to the chest wall, that is, those within half of the diameter of the conical collimator, a semicircular version of the collimator may be constructed to visualize this part of the breast. While possessing only half the sensitivity of the full conical collimator, such a collimator will still yield a gain in sensitivity, such as a five-fold gain, relative to a conventional collimator, and will permit biopsies of lesions close to the chest wall or in the axilla tail.

It will be appreciated that the foregoing collimator design is applicable not only to MBI systems, but to other nuclear medicine-based imaging systems, such as breast-specific gamma imaging ("BGSI") systems.

The present invention has been described in terms of one or more preferred embodiments, and it should be appreciated that many equivalents, alternatives, variations, and modifications, aside from those expressly stated, are possible and within the scope of the invention.

The invention claimed is:

1. A molecular breast imaging (MBI) system structured to be operable in first and second modes of operation, the first mode of operation including an MBI mode and the second mode of operation including one of ultrasound imaging and MBI-guided biopsy, said system comprising:
    a support structure arranged proximate to an examination region;
    a first detector head coupled to the support structure to extend along a first portion of the examination region and including:
        a first gamma ray detector supported by the support structure and extending to define a first imaging plane proximate to the examination region;
        a first collimator extending substantially coplanar with the first imaging plane and arranged between examination region and the first detector;

a second detector head coupled to the support structure to extend along a second portion of the examination region and including:
  a second gamma ray detector supported by the support structure and extending to define a second imaging plane proximate to the examination region;
  a second collimator extending coplanar with the second imaging plane and arranged between examination region and the second detector;
a compression plate being operably coupled and adjacent to the first detector head; and
an adjustable coupling arranged between the first detector head and the support structure to permit movement of the first detector head between a first position and a second position such as to keep the compression plate in place during a conversion of the system from the first mode of operation to the second mode of operation, wherein said conversion is enabled by said movement, wherein the first position is a position in which the first detector head is directly opposed to the second detector head, and a second position is a position in which the first detector head is not directly opposed to the second detector head.

2. The molecular breast imaging system as recited in claim 1, in which at least one of the following conditions is satisfied:
when the first detector head is in the first position, the first imaging plane extends parallel to the second imaging plane;
when the first detector head is in the second position, the first imaging plane extends perpendicular to the second imaging plane.

3. The molecular breast imaging system as recited in claim 1, in which the adjustable coupling includes a pivot defining a rotational axis to permit the first detector head to rotate about the rotational axis to move the first detector head between the first position and the second position, wherein a range of angle of rotation is up to 90 degrees.

4. The molecular breast imaging system as recited in claim 3, further comprising the compression plate coupled to the first detector head and configured to remain fixed in the first imaging plane when the first detector head is moved between the first position and the second position.

5. The molecular breast imaging system as recited in claim 4 in which the compression plate includes at least one of an acoustic coupling plate and a biopsy grid plate.

6. The molecular breast imaging system as recited in claim 1 in which the adjustable coupling includes a support arm configured to slidably move the first detector head along a direction lying in the first imaging plane to permit the first detector head to move along the direction to move the first detector head between the first position and the second position.

7. The molecular breast imaging system as recited in claim 6 further comprising another adjustable coupling arranged between the second detector head and the support structure to permit movement of the second detector head between a first position with the second detector head directly opposed to the first detector head and a second position with the second detector head not directly opposed to the first detector head.

8. The molecular breast imaging system as recited in claim 7 in which the another adjustable coupling includes another support arm configured to slidably move the second detector head along another direction lying in the second imaging plane to permit the second detector head to move along the another direction to move the second detector head between the first position and the second position.

9. The molecular breast imaging system as recited in claim 6 further comprising a compression plate coupled to the first detector head and extending along a direction lying in the first imaging plane and away from a periphery of the first detector head, the compression plate being arranged so as to not be in contact with the examination region when the first detector head is in the first position and to be in contact with the examination region when the first detector head is in the second position.

10. The molecular breast imaging system as recited in claim 1, in which the second collimator includes a first collimator section having multiple collimator holes extending along a first direction and a second collimator section having multiple collimator holes extending along a second direction.

11. The molecular breast imaging system as recited in claim 10 in which:
the first collimator section is a parallel-hole collimator section and the first direction is perpendicular to the second imaging plane; and
the second collimator section is a slant-hole collimator section and the second direction is angled with respect to the second imaging plane at an angle between zero and ninety degrees.

12. The molecular breast imaging system as recited in claim 11 in which the parallel-hole collimator section has a circular outer periphery, and the slant-hole collimator section is annular in shape and extends about the outer periphery of the parallel-hole collimator section.

13. The molecular breast imaging system as recited in claim 10 in which the second detector head further comprises a collimator sleeve coupled to the second gamma ray detector and configured to interchangeably receive the second collimator.

14. A molecular breast imaging (MBI) system structured to be operable in first and second modes of operation, the first mode of operation including an MBI mode and the second mode of operation including one of ultrasound imaging and MBI-guided biopsy, said system comprising:
a support structure;
a first detector head coupled to the support structure, the first detector head including:
  a first gamma ray detector;
  a first collimator;
a compression plate operably coupled and adjacent to the first detector head; and
a second detector head coupled to the support structure and configured to move between a first position and a second position relative to the first detector head,
  such as to keep the compression plate fixed during a movement of the second detector head between the first and second positions, said movement enabling a conversion of the system from the first mode of operation to the second mode of operation, and
  such that, in the first position, the second detector head is directly opposed to the first detector head, and, in the second position, the second detector head is not directly opposed to the first detector head,
wherein the second detector head includes a second gamma ray detector and a second collimator.

15. The molecular breast imaging system as recited in claim 14, further comprising a pivot defining a rotational axis to permit the second detector head to rotate about the rotational axis to move the second detector head between the first position and the second position that are separated by any angle a value of which is between zero and ninety degrees.

16. The molecular breast imaging system as recited in claim 15, further comprising a compression plate coupled to the second detector head and arranged between the first detector head and the second detector head, the compression plate being configured to remain in a fixed position while the second detector head is moved between the first position and the second position, the fixed position defining a plane that is parallel to an imaging plane of said system.

17. A medical imaging (MBI) system structured to be operable in first and second modes of operation, the first mode of operation including an MBI mode and the second mode of operation including one of ultrasound imaging and MBI-guided biopsy, said system comprising:
  a detector extending to define an imaging surface, and configured to receive radiation from a radiation source within a tissue of interest and produce, in response thereto, an image signal;
  a collimator positioned proximate the detector, the collimator including:
    a first collimation region having multiple collimator holes that extend along a first direction with respect to a direction that is normal to the imaging surface proximate the first collimation region, such that radiation from the radiation source is received along the first direction by a first region of the detector;
    a second collimation region having multiple collimator holes each of which extends along a respectively corresponding second direction that is inclined by the same angle with respect to the first direction such that radiation from the radiation source is received along the second direction by a second region of the detector, and in which the second direction is different from the first direction;
  a processor operably coupled to the detector and configured to receive the image signal and to identify a depth of the radiation source in the tissue of interest using the received image signal, the septa geometry of the first collimation region, and the septa geometry of the second collimation region.

18. The medical imaging system as recited in claim 17 in which at least one of:
  the second collimation region extends about an outer periphery of the first collimation region; and
  the first collimation region is circular and the second collimation region is annular.

19. The medical imaging system as recited in claim 17, in which the first direction is substantially parallel to the direction that is normal to the imaging surface proximate the first collimation region, and in which a plurality of lines along second directions, which respectively correspond to the multiple collimation holes of the second collimation region, form a cone.

20. The medical imaging system as recited in claim 19, in which the first collimation region is circular, the second collimation region is annular, and said second directions are selected such as to define an apex of said cone on an axis that passes through a center collimation region perpendicularly to the imaging surface.

* * * * *